United States Patent [19]
Murray et al.

[11] Patent Number: 5,986,030
[45] Date of Patent: Nov. 16, 1999

[54] FLUORESCENT WATER SOLUBLE POLYMERS

[75] Inventors: Patrick G. Murray, Yorkville; Wesley L. Whipple, Naperville, both of Ill.

[73] Assignee: Nalco Chemical Company, Naperville, Ill.

[21] Appl. No.: 08/843,407

[22] Filed: Apr. 15, 1997

[51] Int. Cl.$^6$ .................................................. C08F 224/00
[52] U.S. Cl. ......................... 526/268; 526/259; 526/260; 526/280
[58] Field of Search .................... 526/258, 259, 526/260, 266, 268, 280, 284

[56] References Cited

U.S. PATENT DOCUMENTS

| | | | |
|---|---|---|---|
| 4,783,314 | 11/1988 | Hoots et al. | 422/3 |
| 4,813,973 | 3/1989 | Winnik et al. | |
| 4,999,456 | 3/1991 | Fong | 526/304 |
| 5,043,406 | 8/1991 | Fong | 526/304 |
| 5,128,419 | 7/1992 | Fong et al. | 525/351 |
| 5,171,450 | 12/1992 | Hoots | 210/701 |
| 5,408,022 | 4/1995 | Imazato | 526/259 |
| 5,435,969 | 7/1995 | Hoots | 422/14 |

FOREIGN PATENT DOCUMENTS 1 141 147  1/1969  Japan .

OTHER PUBLICATIONS

The Use of Coumarin Derivatives in the Preparation of Fluorescence–Labeled Poly[N–(2–Hydroxypropyl) Methacrylamide], *Collection Czechoslov. Chem Common*, vol. 45, 1980, pp. 727–731.

*Primary Examiner*—Christopher Henderson
*Attorney, Agent, or Firm*—Margaret M. Brumm; Thomas M. Breininger

[57] ABSTRACT

A cationic water-soluble polymer comprising from 0.001 to 10 mole percent of a repeating mer unit represented by the formula

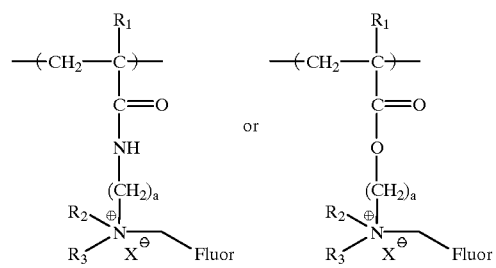

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylamninoethyl methacrylate benzyl chloride quaternary salt, methacrylamidopropyl trimethyl ammonium chloride and acrylamidopropyl trimethyl ammonium chloride.

Preferably, fluor is selected from the group consisting of 1-(substituted)naphthalene, 9-(substituted)anthracene, 2-(substituted)quinoline monohydrochloride, 2-(substituted) benzimidazole, 5-(substituted)fluorescein, 4-(substituted) coumarin and 3-(substituted)-6,7-dimethoxy-1-methyl-2(1H)-quinoxazolinone.

Most preferably, fluor is a coumarin derivative.

Monomers of the structures described above are also disclosed. Moreover, a method for determining the efficiency of water-soluble polymeric treating agents utilizing the above-mentioned polymers is also disclosed.

5 Claims, No Drawings

FLUORESCENT WATER SOLUBLE POLYMERS

FIELD OF THE INVENTION

A cationic water-soluble polymer comprising from 0.001 to 10.0 mole percent of a repeating mer unit represented by the formula

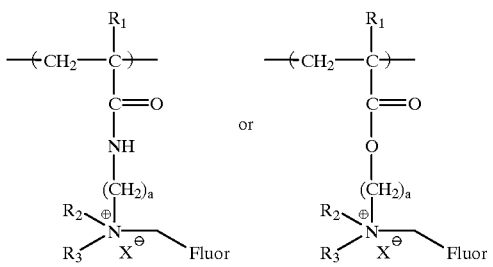

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamnide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride.

Preferably, fluor is selected from the group consisting of 1-(substituted)naphthalene, 9-(substituted)anthracene, 2-(substituted)quinoline monohydrochloride, 2-(substituted)benzimidazole, 5-(substituted)fluorescein, 4-(substituted) coumarin and 3-(substituted)-6,7-dimethoxy-1-methyl-2 (1H)-quinoxazolinone.

Most preferably, fluor is a coumarin derivative.

Monomers of the structures described above are also disclosed. Moreover, a method for determining the efficiency of water-soluble polymeric treating agents utilizing the above-mentioned polymers is also disclosed.

BACKGROUND OF THE INVENTION

In many fields that employ polymers it may be desirable to tag or mark such polymers to facilitate monitoring thereof. By the term "monitoring" is meant herein any type of tracing or tracking to determine the location or route of the polymers, and any type of determination of the concentration or amount of the polymer at any given site, including singular or intermittent or continuous monitoring. For instance, it may be desirable to monitor water treatment polymers in water systems, particularly industrial water systems, or to monitor polymers that may be present in waste fluids before disposal, particularly industrial waste fluids, or to monitor the polymer used for down-hole oil well applications, particularly the route taken after introduction down-hole, or to monitor polymers that may be present in fluids used to wash a manufactured product, for instance a polymer-coated product, to determine the amount of polymer washed or leached therefrom. By fluids or liquids as used herein generally is meant aqueous, non-aqueous, and mixed aqueous/non-aqueous fluid systems. As seen from the above list of possible applications of polymer monitoring, the purpose of such monitoring may be to trace or track or determine the level of the polymer itself, or to trace or track or determine the level of some substance in association with the polymer, or to determine some property of the polymer or substance in association with the polymer, for instance its leachability.

Conventional techniques for monitoring polymers are generally time-consuming and labor intensive, and often require the use of bulky and/or costly equipment. Most conventional polymer analysis techniques require the preparation of calibration curves for each type of polymer employed, which is time-consuming and laborious, particularly when a large variety of polymer chemistries are being employed, and the originally prepared calibration curves lose their accuracy if the polymer structures change, for instance an acrylic acid ester mer unit being hydrolyzed to an acrylic acid mer unit. Direct methods wherein the level of functional groups present in a polymer is determined analytically are generally not practical for industrial use, particularly when it is desired to monitor a polymer on a frequent or continuous basis, or when rapid monitoring results are needed. Indirect methods of polymer monitoring may provide more rapid results using simpler techniques, but in many instances faster and/or more accurate determinations are desirable.

Polymers tagged with pendant fluorescent groups are generally easily monitored, even when present at low concentrations. In theory, the fluorescence quantum efficiency and molar extinction coefficient of the fluorescent group need only be large enough to generate an acceptable signal to noise ratio for the tagged polymer in the matrix in which detection occurs. What is required in terms of quantum efficiency and molar extinction to detect fluorescently tagged polymer will depend upon background fluorescence of the matrix at the wavelength that emission is being monitored, the intensity of the excitation source, and the efficiency of the emission collection device (detector). In practice, the incorporation of a fluorescent species in a polymer in the amount of one weight percent or less is desirable; this should be sufficient to permit the detection of polymer at ppm or ppb concentration levels, provided the fluorescent quantum yield and the light absorbance molar extinction coefficient of the fluorescent tagging agent are not significantly adversely affected by its attachment to the polymer.

Some polymers tagged with pendant fluorescent groups are known. A process for preparing a cross-linkable fluorescent compound bonded polymer from the copolymerization of a fluorescent compound wherein an acrylamide moiety and the aromatic fluorescing moiety are directly linked through an amide bond to the aromatic ring is disclosed in Japanese Patent No. 1,141,147. Other fluorescent acrylamide based polymers are disclosed in U.S. Pat. Nos. 5,043,406 and 4,999,456. Polymers tagged with pendant fluorescent groups have been prepared by the transamidation derivatization of the pre-existing polymers having carbonyl-type pendant groups in U.S. Pat. No. 5,128,419. Another post-polymerization modification of a polyacrylamide with a fluorescing moiety is disclosed in U.S. Pat. No. 4,813,973. The preparation of certain vinylic coumarin derivatives is disclosed in *Collection Czechoslov. Chem Common*, Vol. 45, 1980, pgs. 727–731. However, none of these disclosures cite the monomers and polymers of the instant invention.

A specific example of the utility of a polymer tagged with pendant fluorescent groups may be drawn from the field of solids/liquid separation.

In the water treatment field of solids/liquid separation, suspended solids are removed from water by a variety of processes, including without limitation, sedimentation, straining, flotation, filtration, coagulation, flocculation, emulsion breaking and the like. Additionally, after suspended solids are removed from the water they must often be dewatered so that they may be further treated or properly disposed. Liquids treated for solids removal often have as little as several parts per billion of suspended solids or dispersed oils may contain large amounts of suspended solids or oils. Solids being dewatered may contain anywhere from 0.25 weight percent solids, to 40 or 50 weight percent solids material. So called liquid solids separation processes are designed to remove solids from water, or, conversely and depending upon the desired component, liquids from solids.

While strictly mechanical means have been used to effect solids/liquid separation, modem methods often rely on mechanical separation techniques which are augmented by synthetic and natural cationic polymeric materials to accelerate the rate at which solids can be removed from water. These processes include treatment of raw water with cationic coagulant polymers which settle suspended inorganic particulates and make the water usable for industrial or municipal purposes. Other examples of these processes include the removal of colored soluble species from paper mill effluent wastes, the use of organic flocculant polymers to flocculate industrial and municipal waste materials, recovering a sludge and emulsion breaking.

Regarding the mechanism of separation processes, particles in nature have either a cationic or anionic charge. Accordingly, these particles often are removed by a water soluble coagulant or flocculent polymer having a charge opposite to that of the particles. This is referred to as polyelectrolyte enhanced liquid/solids separation processes, wherein a water soluble or dispersible ionically charged polymer is added to neutralize the charged particles or emulsion droplets to be separated. The dosage of these polymers is critical to the performance of the process. Too little ionically charged polymer, and the suspended particles will not be charge neutralized and will thus still repel each other. Too much polymer, and the polymer will be wasted, or worse, flocculation will be adversely affected.

If the polyelectrolyte or ionically charged polymer being added is very effective for the given process, the polyelectrolyte that leaves with the water fraction generally represents an overdosage. More polyelectrolyte was added than required. If the polyelectrolyte being added is not very effective for the given process, significant amounts of polymer may leave the process with the water fraction as an indication of the polymers performance deficiencies. In either instance, a determination of the amount of polyelectrolyte that leaves a separation process with the filtrate or water fraction would be extremely beneficial. An effective polyelectrolyte should be added to a separation process in an amount just at or above that consumed by attachment to the solids or oil surfaces. Whether the dosage selected approaches this optimal dosage could be determined, and the dosage adjusted if necessary, if the level of the polyelectrolyte in the filtrate could be easily monitored. A less effective polyelectrolyte could be readily detected, and the polyelectrolyte selection changed if the level of the polyelectrolyte in the filtrate could be easily monitored.

Monitoring the concentration of polyelectrolyte in the filtrate is a formidable task not well suited to industrial applications. Analytical techniques such as colloid titration are complicated and time consuming and do not permit a real time result. Electronic instrumentation to determine charge is available, but such devices are expensive, and do not differentiate between charge associated with a polymer, or charge from other sources, including the water, solids, or other constituent in the effluent. Time consuming measurements are inefficient since the characteristics of a waste stream or emission may vary considerably with time.

The use of fluorescence emission spectroscopy to determine the concentration of a fluorescent chemical species is extremely rapid and sensitive, but the species being monitored must be fluorescent. A typical polyelectrolyte is not fluorescent or is not sufficiently fluorescent for monitoring by emission spectroscopy. Since the polyelectrolyte in its performance is consumed in the sense that it attaches to the solids and/or oils and is separated from the water therewith, adding a fluorescent signature chemical or tracer that follows the water would not reveal what fraction of the polyelectrolyte has been consumed, even if the concentration of the tracer can be correlated to polyelectrolyte dosage.

While determining polyelectrolyte dosage, for instance by adding a tracer in known proportion to the polyelectrolyte and monitoring the tracer concentration to determine if the target dosage or feed rate is being met, may in and of itself be of significant assistance, a water-soluble totally inert tracer is an indicator of only the theoretical zero-consumption concentration of the polyelectrolyte in the filtrate, and not the actual filtrate concentration of the polyelectrolyte. A signature chemical or tracer that itself preferentially follows the solids and/or oil likewise is not an indicator of polyelectrolyte consumption and hence polyelectrolyte performance.

It is therefore an object of this invention to provide a process for monitoring a polyelectrolyte water treatment chemical that is consumed in its performance, preferentially associating with one phase in a multiphase system.

It is an object of the present invention to monitor a polyelectrolyte that preferentially associates with one phase of a multiphase system by determining the extent of such preferential association.

It is an object of the present invention to determine the extent of preferential phase association of polyelectrolyte in a multiphase system using a technique that is rapid and sensitive. It is an object of the present invention to determine the extent of preferential phase association of a polyelectrolyte in a multiphase system using a technique that can be employed on a semi-continuous or continuous basis.

It is an object of the present invention to determine the extent of preferential phase association of a polyelectrolyte in a multiphase system using a technique that can be employed on line. It is an object of the present invention to determine the extent of preferential phase association of a polyelectrolyte in a multiphase system using a technique that determines the concentration of the polyelectrolyte in the non-preferred phase. These and other objects of the present invention are described in detail below.

The ability to exploit fluorescent polymers and to obtain economic benefits from their deployment depends upon the ability to detect fluorescence contributed by the polymer over any background incidental to the application. If this necessary condition can be achieved, and the increase in observed fluorescence as a finction of polymer dose corresponds to optimal product performance, then a useful tool has been developed. These and other objects are provided by the present invention which is described in more detail below.

SUMMARY OF THE INVENTION

A cationic water-soluble polymer comprising from 0.001 to 10.0 mole percent of a repeating mer unit represented by the formula

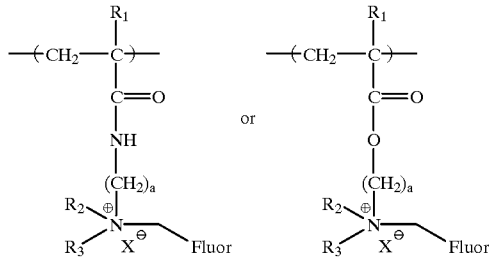

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quatemnary salt, methacrylamidopropyl trimethyl ammonium chloride and acrylamidopropyl trimethyl ammonium chloride.

Preferably, fluor is selected from the group consisting of 1-(substituted) naphthalene, 9-(substituted)anthracene, 2-(substituted)quinoline monohydrochloride, 2-(substituted) benzimidazole, 5-(substituted)fluorescein, 4-(substituted) coumarin and 3-(substituted)-6,7-dimethoxy-1-methyl-2 (1H)-quinoxazolinone.

Most preferably, fluor is a coumarin derivative.

Monomers of the structures described above are also disclosed. Moreover, a method for determining the efficiency of water-soluble polymeric treating agents utilizing the above-mentioned polymers is also disclosed.

DESCRIPTION OF THE INVENTION

The present invention generally relates to polymerization of polymers with fluorescent monomers to obtain fluorescent polymers. Uses for polymers thus formed are also described herein.

The invention is a cationic water-soluble polymer comprising from 0.001 to 10 mole percent of a repeating mer unit represented by the formula

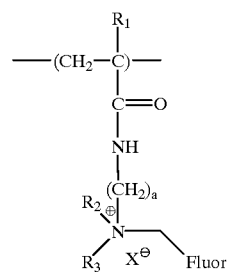

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride. Fluor may be selected from the group consisting of 1-(substituted) naphthalene, 9-(substituted)anthracene, 2-(substituted) quinoline monohydrochloride, 2-(substituted) benzimidazole, 5-(substituted)fluorescein, 4-(substituted) coumarin and 3-(substituted)-6,7-dimethoxy-1-methyl-2 (1H)-quinoxazolinone. Moreover, the polymer described above may be selected from the group consisting of emulsion, solid, dispersion and solution polymers.

The invention is also a cationic water-soluble polymer comprising from 0.001 to 10 mole percent of a repeating mer unit represented by the formula

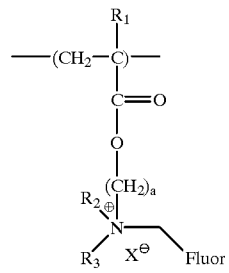

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride. Fluor may be selected from the group consisting of 1-(substituted) naphthalene, 9-(substituted)anthracene, 2-(substituted) quinoline monohydrochloride, 2-(substituted) benzimidazole, 5-(substituted)fluorescein, 4-(substituted) coumarin and 3-(substituted)-6,7-dimethoxy-1-methyl-2 (1H)-quinoxazolinone. Moreover, the polymer may be selected from the group consisting of emulsion, solid, dispersion and solution polymers.

Another embodiment of this invention is a cationic water-soluble polymer comprising from 0.001 to 10 mole percent of a repeating mer unit represented by the formula

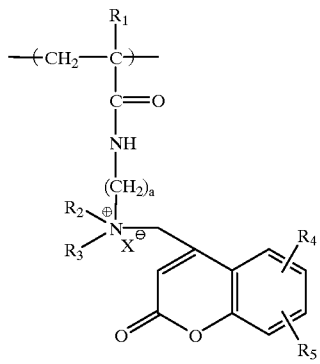

wherein a is an integer of from 1 to 10, $R_1$ is selected from the group consisting of hydrogen and methyl groups, $R_2$ and $R_3$ are methyl groups, $R_4$ and $R_5$ are selected from the group consisting of hydrogen, hydroxy, methoxy, ethoxy, amino, dimethylamino, diethylamino and acetoxy groups, and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride. As mentioned above, a may be an integer of from 2–4. Furthermore, the polymer may be selected from the group consisting of emulsion, solid, dispersion and solution polymers.

In still another embodiment, the invention is a cationic water-soluble polymer comprising from 0.001 to 10 mole percent of a repeating mer unit represented by the formula

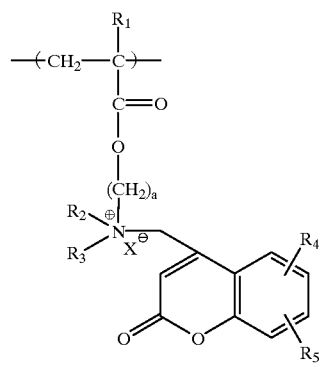

wherein a is an integer of from 1 to 10, $R_1$ is selected from the group consisting of hydrogen and methyl groups, $R_2$ and $R_3$ are methyl groups, $R_4$ and $R_5$ are selected from the group consisting of hydrogen, hydroxy, methoxy, ethoxy, amino, diethylamino, dimethylamino and acetoxy groups, and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride. As described above, a may be an integer of from 2–4. Moreover, the polymer may be selected from the group consisting of emulsion, solid, dispersion and solution polymers.

In another embodiment, the invention is a cationic water-soluble polymer comprising from 0.001 to 10 mole percent of a repeating mer unit represented by the formula

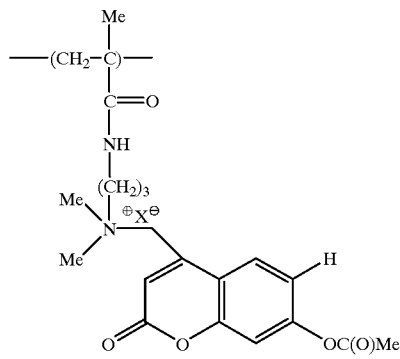

wherein X is selected from the group consisting of bromide, iodide and chloride ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride. Moreover, the polymer may be selected from the group consisting of emulsion, solid, dispersion and solution polymers.

Another embodiment of this invention is a cationic water-soluble polymer comprising from 0.001 to 10 mole percent of a repeating mer unit represented by the formula

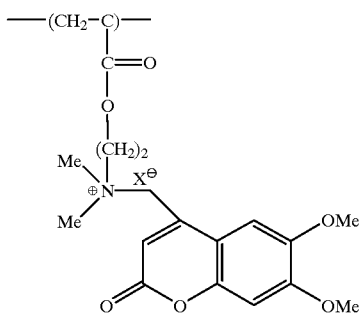

wherein X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride. Moreover, the polymer may be selected from the group consisting of emulsion, solid, dispersion and solution polymers.

Yet another embodiment of this invention is a monomer of the formula

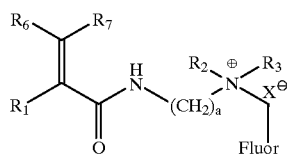

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions. Fluor may be selected from the group consisting of 1-(substituted)naphthalene, 9-(substituted)anthracene, 2-(substituted)quinoline monohydrochloride, 2-(substituted)benzimidazole, 5-(substituted)fluorescein, 4-(substituted)coumarin and 3-(substituted)-6,7-dimethoxy-1-methyl-2(1H)-quinoxazolinone.

The invention is also a monomer of the formula

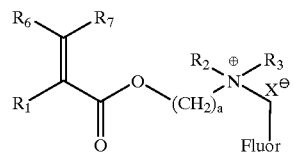

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions. Fluor may be selected from the group consisting of 1-(substituted)naphthalene, 9-(substituted)anthracene, 2-(substituted)quinoline monohydrochloride, 2-(substituted)benzimidazole, 5-(substituted)fluorescein, 4-(substituted)coumarin and 3-(substituted)-6,7-dimethoxy-1-methyl-2(1H)-quinoxazolinone.

The invention is also a monomer of the formula

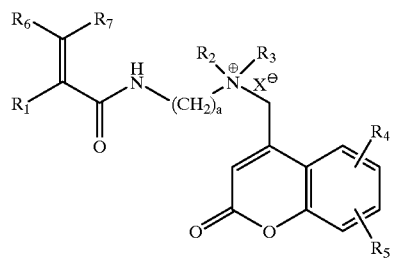

wherein a is an integer of from 1 to 10, $R_1$ is selected from the group consisting of hydrogen and methyl groups, $R_2$ and $R_3$ are methyl groups, $R_4$ and $R_5$ are selected from the group consisting of hydrogen, hydroxy, methoxy, ethoxy, amino, dimethylamino, diethylamino and acetoxy groups, $R_6$ and $R_7$ are hydrogen, and X is selected from the group consisting of chloride, iodide and bromide ions. In this monomer, a may be an integer of from 2–4.

The invention is also a monomer of the formula

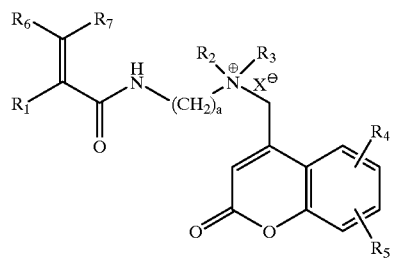

wherein a is an integer of from 1 to 10, $R_1$ is selected from the group consisting of hydrogen and methyl groups, $R_2$ and $R_3$ are methyl groups, $R_4$ and $R_5$ are selected from the group consisting of hydrogen, hydroxy, methoxy, ethoxy, amino, dimethylamino, diethylamino and acetoxy groups, $R_6$ and $R_7$ are hydrogen, and X is selected from the group consisting of chloride, iodide and bromide ions. For this monomer, a may be an integer of from 2–4.

The invention is also a monomer of the formula

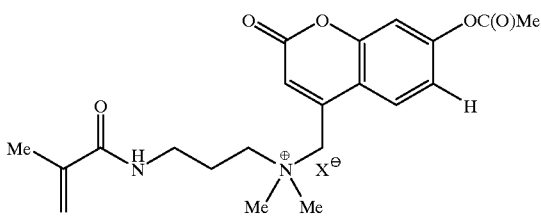

wherein X is selected from the group consisting of bromide, iodide and chloride ions.

Moreover, the invention is also a monomer of the formula

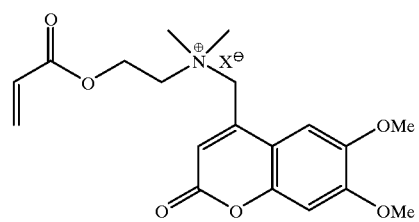

wherein X is selected from the group consisting of bromide, iodide and chloride ions.

In another embodiment, the invention is a method for determining the efficiency of a water-soluble polymeric treating agent added to water confined in a once-through system, comprising the steps of:

a) combining a predetermined amount of said water-soluble polymeric treating agent with a predetermined effective indicating amount of a water-soluble indicator polymer having from 0.001 to 10 mole percent of a repeating mer unit represented by the formula

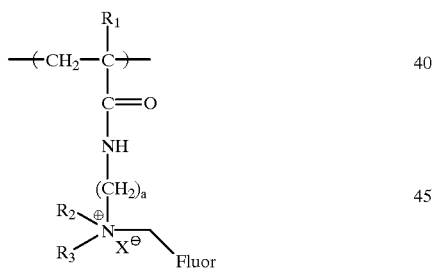

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride;

b) adding said water-soluble indicator polymer and said water-soluble polymeric treating agent to said water;

c) removing an aliquot of water treated according to step b);

d) analyzing the emissivity of said water as a measure of the concentration of said indicator polymer;

e) determining from the analysis of step d) that a change in concentration of said indicator polymer from said predetermined amount has occurred;

f) determining that a proportional change in said amount of said polymeric treating agent has occurred; and g) adjusting the concentration of said polymeric treating agent accordingly. For the practice of this method, fluor may be selected from the group consisting of 1-(substituted)naphthalene, 9-(substituted)anthracene, 2-(substituted)quinoline monohydrochloride, 2-(substituted)benzimidazole, 5-(substituted) fluorescein, 4-(substituted)coumarin and 3-(substituted)-6,7-dimethoxy-1-methyl-2(1H)-quinoxazolinone. Furthermore, the polymer may be selected from the group consisting of emulsion, solid, dispersion and solution polymers. Herein, the terms indicator polymer, tagged polymer and fluorescent polymer are used interchangeably, and are meant to describe the polymers of the instant invention which fluoresce as a result of incorporation of a fluorescent moiety during polymerization. Also, as described herein, the water-soluble polymeric treating agent can be the same as the water-soluble indicator polymer. For example a poly(acrylic acid) polymer tagged as described herein can be used as the treating agent and as the indicator polymer. Alternatively, poly(acrylic acid) would be used as the polymeric treating agent and the corresponding tagged poly(acrylic acid) would be the indicator polymer. However, if the two are different, a minimally detectable amount of the water-soluble indicator polymer would be utilized in conjunction with the untagged water-soluble polymeric treating agent. As used herein, the term water-soluble polymeric treating agent refers to polymers which are added to aqueous systems for the purpose of scale control, corrosion inhibition, dispersing, flocculating, coagulating and thickening among others. The waters of once through systems may be either natural or industrial waters. The industrial waters may be municipal wastewaters, chemical processing wastewaters, boiler water, cooler water and water utilized in papermaking and mining applications among others. The term predetermined amount, in reference to the water-soluble polymeric treating agent, refers to an amount required by the system to effect a particular treatment. For example, if the water is a boiler water, the predetermined amount would be the effective corrosion-preventing amount of polymer required by that particular aqueous system to prevent corrosion. As used herein, the term predetermined effective indicating amount refers to a minimal amount which can be detected by a fluorescent technique (above the native fluorescence of the aqueous system being treated). The water-soluble polymeric treating agent and the water-soluble polymeric indicator may be blended prior to addition, or added individually in sequential fashion. Once they have been added to the system, a portion of that treated water can be removed for analysis. As utilized herein, the term "analyzing the emissivity" refers to monitoring by a fluorescent technique. Such techniques, and required calculations to correlate fluorescence to concentration are described in U.S. Pat. Nos. 5,435,969; 5,171,450 and 4,783,314 among others. U.S. Pat. Nos. 5,435,969; 5,171,450 and 4,783,314 are incorporated herein by reference. By the term "adjusting the concentration of said polymeric treating agent accordingly" is meant that the amount of the water soluble polymeric treating agent is adjusted based on some significant change in the fluorescence measurement. The actual fluorescence measurement may either increase or decrease depending on the application, as a function of polymer dosage, or the relative changes in the fluorescence measurement may either become larger or smaller as a function of polymer dosage. When such changes occur at or near the optimum polymer dosage as represented by some other parameter of interest (for example drainage, turbidity reduction, color removal, etc.) then the trends in the fluorescence measurement can be used to determine and maintain the proper dosage of the polymeric treating agent for the particular parameter of interest. The method is particularly suited to applications where such instantaneous feedback could be provided by an in-line fluorescence monitoring device would be used as part of a system to control a polymer feeding pump, for example, wherein the polymer dosage is increased or decreased depending on the response from the fluorescence measurement device.

The invention is also a method for determining the efficiency of a water-soluble polymeric treating agent added to water confined in a once-through system, comprising the steps of:

a) combining a predetermined amount of said water-soluble polymeric treating agent with a predetermined effective indicating amount of a water-soluble indicator polymer having from 0.001 to 10 mole percent of a repeating mer unit represented by the formula

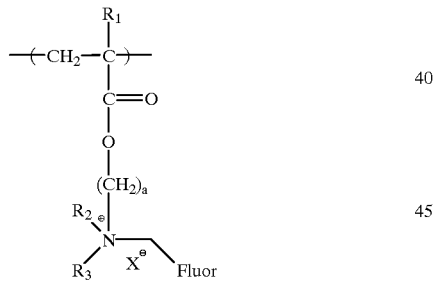

wherein a is an integer of from 1 to 10, $R_1$ is selected from the group consisting of hydrogen and methyl groups, $R_2$ and $R_3$ are methyl groups, fluor is a fluorescing moiety and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride;

b) adding said water-soluble indicator polymer and said water-soluble polymeric treating agent to said water;

c) removing an aliquot of the water treated according to step b);

d) analyzing the emissivity of said water as a measure of the concentration of said indicator polymer;

e) determining from the analysis of step d) that a change in concentration of said indicator polymer from said predetermined amount has occurred;

f) determining that a proportional change in said amount of said polymeric treating agent has occurred; and g) adjusting the concentration of said polymeric treating agent accordingly. For the practice of this invention, fluor may be selected from the group consisting of 1-(substituted)naphthalene, 9-(substituted)anthracene, 2-(substituted)quinoline monohydrochloride, 2-(substituted) benzimidazole, 5-(substituted) fluorescein, 4-(substituted)coumarin and 3-(substituted)-6,7-dimethoxy-1-methyl-2(1H)-quinoxazolinone. Moreover, the polymer may be selected from the group consisting of emulsion, solid, dispersion and solution polymers.

The invention is also a method for determining the efficiency of a water-soluble polymeric treating agent added to water confined in a once-through system, comprising the steps of:

a) combining a predetermined amount of said water-soluble polymeric treating agent with a predetermined effective indicating amount of a water-soluble indicator polymer having from 0.001 to 10 mole percent of a repeating mer unit represented by the formula

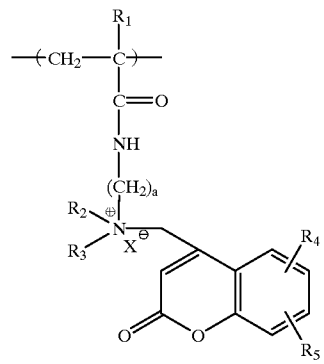

wherein a is an integer of from 1 to 10, $R_1$ is selected from the group consisting of hydrogen and methyl groups, $R_2$ and $R_3$ are methyl groups, $R_4$ and $R_5$ are selected from the group consisting of hydrogen, hydroxy, methoxy, ethoxy, amino, dimethylamino, diethylamino and acetoxy groups, and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride;

b) adding said water-soluble indicator polymer and said water-soluble polymeric treating agent to said water;

c) removing an aliquot of the water treated according to step b);

d) analyzing the emissivity of said water as a measure of the concentration of said indicator polymer;

e) determining from the analysis of step d) that a change in concentration of said indicator polymer from said predetermined amount has occurred;

f) determining that a proportional change in said amount of said polymeric treating agent has occurred; and g) adjusting the concentration of said polymeric treating agent accordingly. For the practice of this invention, for the indicator polymer, a may be an integer of from 2–4. Furthermore, the indicator polymer may be selected from the group consisting of emulsion, solid, dispersion and solution polymers.

The invention is also a method for determining the efficiency of a water-soluble polymeric treating agent added to water confined in a once-through system, comprising the steps of:

a) combining a predetermined amount of said water-soluble polymeric treating agent with a predetermined effective indicating amount of a water-soluble indicator polymer having from 0.001 to 10 mole percent of a repeating mer unit represented by the formula

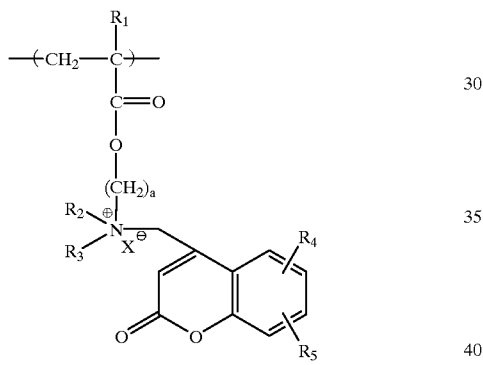

wherein a is an integer of from 1 to 10, $R_1$ is selected from the group consisting of hydrogen and methyl groups, $R_2$ and $R_3$ are methyl groups, $R_4$ and $R_5$ are selected from the group consisting of hydrogen, hydroxy, methoxy, ethoxy, amino, diethylamino, dimethylamino and acetoxy groups, and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride;

b) adding said water-soluble indicator polymer and said water-soluble polymeric treating agent to said water;

c) removing an aliquot of the water treated according to step b);

d) analyzing the emissivity of said water as a measure of the concentration of said indicator polymer;

e) determining from the analysis of step d) that a change in concentration of said indicator polymer from said predetermined amount has occurred;

f) determining that a proportional change in said amount of said polymeric treating agent has occurred; and g) adjusting the concentration of said polymeric treating agent accordingly. For the practice of the above method, for the indicator polymer, a may be an integer of from 2–4. Furthermore, the polymer may be selected from the group consisting of emulsion, solid, dispersion and solution polymers.

In still another embodiment, the invention is a method for determining the efficiency of a water-soluble polymeric treating agent added to water confined in a once-through system, comprising the steps of:

a) combining a predetermined amount of said water-soluble polymeric treating agent with a predetermined effective indicating amount of a water-soluble indicator polymer having from 0.001 to 10 mole percent of a repeating mer unit represented by the formula

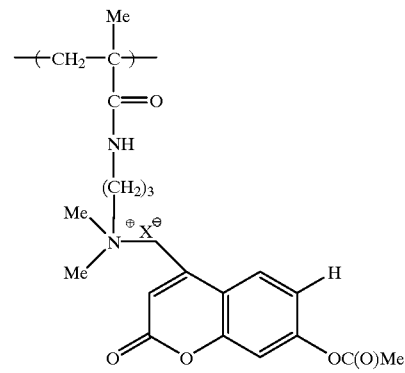

wherein X is selected from the group consisting of bromide, iodide and chloride ions and wherein the polymer also contains from 90 to 99.99 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride;

b) adding said water-soluble indicator polymer and said water-soluble polymeric treating agent water to said water;

c) removing an aliquot of the water treated according to step b);

d) analyzing the emissivity of said water as a measure of the concentration of said indicator polymer;

e) determining from the analysis of step d) that a change in concentration of said indicator polymer from said predetermined amount has occurred;

f) determining that a proportional change in said amount of said polymeric treating agent has occurred; and g) adjusting the concentration of said polymeric treating agent accordingly. The indicator polymer may be selected from the group consisting of emulsion, solid, dispersion and solution polymers.

The invention is also a method for determining the efficiency of a water-soluble polymeric treating agent added to water confined in a once-through system, comprising the steps of:

a) combining a predetermined amount of said water-soluble polymeric treating agent with a predetermined effective indicating amount of a water-soluble indicator polymer having from 0.001 to 10 mole percent of a repeating mer unit represented by the formula

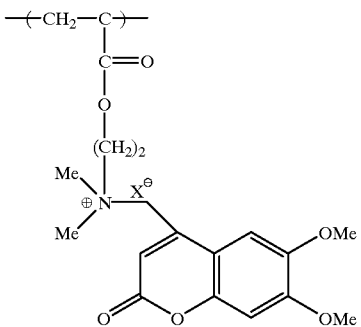

wherein X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamnide, vinyl acetate, dimethylaminoethyl acrylate methyl chloride quatemnary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamnidopropyl trimethyl ammonium chloride;

b) adding said water-soluble indicator polymer and said water-soluble polymeric treating agent to said water;

c) removing an aliquot of the water treated according to step b);

d) analyzing the emissivity of said water as a measure of the concentration of said indicator polymer;

e) determining from the analysis of step d) that a change in concentration of said indicator polymer from said predetermined amount has occurred;

f) determining that a proportional change in said amount of said polymeric treating agent has occurred; and g) adjusting the concentration of said polymeric treating agent accordingly. For the practice of this method, the indicator polymer may be selected from the group consisting of emulsion, solid, dispersion and solution polymers.

The following examples are presented to describe preferred embodiments and utilities of the invention and are not meant to limit the invention unless otherwise stated in the claims appended hereto.

EXAMPLE 1

A quaternary ammonium salt of dimethylaminopropyl-methacrylamide (DMAPMA) and 4-(bromomethyl)-7-acetoxycoumarin was synthesized in the following manner. One gram of 4-(bromomethyl)-7-acetoxycoumarin (available from TCI America; Portland, Oreg.), (3.36 mmol) was charged to a 100 mL round bottom flask equipped with a magnetic stir bar and a reflux condenser. Enough acetone (reagent grade or better) to dissolve the material at reflux was added (about 40 mL). N,N-Dimethylaminopropylmethacrylamide (DMAPMA, available from Rohm Tech. Inc.; Malden, Mass.), 1.43 g (2.5 equivalents) was dissolved in about 10 mL of acetone. 4-Methoxyphenol (available from Aldrich; Milwaukee, Wis.), 20 mg, was added to the DMAPMA/acetone solution, and this solution was added dropwise to the 4-(bromomethyl)-7-acetoxycoumarin using an addition funnel over the course of about 10 minutes. The reaction mixture was maintained at reflux for 2 hours, after which time the solution was allowed to cool to room temperature. Left to stand overnight, the product crystallized from the reaction mixture to form a fine white powder that was easily collected by filtration (1.53 g), and characterized by NMR.

EXAMPLE 2

A quaternary ammonium salt of dimethylaminoethyl acrylate (DMAEA) and 4-(bromomethyl)-6,7-dimethoxycoumarin was synthesized in the following manner.

Dimethylaminoethyl acrylate (DMAEA, available from CPS Chemical Co.; Old Bridge, N.J.), 480 mg, was dissolved in 20 mL of tetrahydrofuran in a 50 mL round bottom flask equipped with a magnetic stir bar. 4-(bromomethyl)-6,7-dimethoxycoumarin, (available from Aldrich; Milwaukee, Wis.), 1.0 g, was added to the reaction flask and the mixture was heated to reflux. Enough dimethylformamide (about 5 mL) to just dissolve all of the reactants at reflux was added to the mixture, and then the mixture was maintained at reflux temperature for 2 hours. After this time, the reaction mixture was allowed to cool to room temperature, and a pale yellow powder precipitated from solution. The powder was collected by filtration (1.2 g), and the structure of the product was verified by NMR.

EXAMPLE 3

A quaternary ammonium salt of N,N-dimethylaminopropylmethacrylamide and 3-(bromomethyl)-6,7-dimethoxy-1-methyl-2(1H)-quinoxazolinone was synthesized in the following manner.

To a 50 mL pear-shaped flask, equipped with a magnetic stir bar, Claisen tube, and condenser, was added 3-(bromomethyl)-6,7-dimethoxy-1-methyl-2(1H)-quinoxazolinone (available from Molecular Probes; Eugene, Oreg.), 25 mg, 0.080 mmol), 0.4 mg of 4-methoxyphenol, and 3.2 ml of acetone. A solution resulted when the mixture was heated to 56° C. N,N-Dimethylaminopropylmethacrylamide (DMAPMA, available from Rohm Tech. Inc.; Malden, Mass.), 44.2 mg (0.26 mmol) was added by syringe to the solution. The resulting mixture was heated for 110 min at 56° C. After 54 min, a white solid was observed in the flask. The reaction mixture was cooled and allowed to stand at room temperature for 120 min. The white solid was isolated by filtration through a sintered glass funnel, then washed with three 2 ml portions of acetone. The DMAPMA-3-(bromomethyl)-6,7-dimethoxy-1-methyl-2(1H)-quinoxazolinone quaternary salt was obtained in 88% yield (34 mg). The structure of the product was confirmed by $^1$H-NMR.

EXAMPLE 4

A quaternary ammonium salt of N,N-dimethylaminopropylmethacrylamide and 5-(bromomethyl) fluorescein was synthesized in the following manner.

To a 25 ml pear-shaped flask, equipped with a magnetic stir bar, Claisen tube, and condenser was added 5-(bromomethyl)fluorescein (available from Molecular Probes, Eugene, Oreg.), 12.1 mg (0.0284 mmol), 1 small crystal of MEHQ, and 1.00 g of dimethylformamide (reagent grade or better). A solution resulted upon stirring. N,N-Dimethylaminopropylmethacrylamide (DMAPMA, available from Rohm Tech. Inc.; Malden, Mass.), 14.5 mg,(0.0845 mmol) was added to the solution. The resulting mixture was heated for 135 minutes at 56° C. The quaternary salt was not isolated, but was used as solution in dimethylformamide (concentration approximately 1.69%).

EXAMPLE 5

A 35 mole % cationic (65/25/10 acrylarnide/DMAEA-BCQ/DMAEA-MCQ) fluorescent dispersion polymer was synthesized by combining 402 g of deionized water, 148 g of a 48.1% aqueous solution of acrylamide, 130 g of an 80% aqueous solution of DMAEA-BCQ (dimethylaminoethyl acrylate benzyl chloride quaternary salt), 37 g of an 80% aqueous solution of DMAEA-MCQ (dimethylaminoethyl acrylate methyl chloride quaternary salt), 15 g of glycerin, 50 g of a DADMAC (diallyldimethyl ammonium chloride)/DMAEA-BCQ copolymer (20% aqueous solution), 0.30 g of ethylene diamine tetraacetic acid, tetra sodium salt, 156 g of ammonium sulfate, and 200 mg of the appropriate fluorescent monomer synthesized according to the procedure described in Example 2. This mixture was heated to 48° C. with vigorous mixing. Upon reaching that temperature, 1.2 g of a 1% aqueous solution of V-50 (2,2'-azobis-(2-amidinopropane) dihydrochloride, available from Wako Chemicals, USA, Inc.; Richmond, Va.) was added and a nitrogen purge was introduced. An additional 2.8 g of a 1% solution of V-50 was added after two hours. The mixture was polymerized for six hours (total) under these conditions, cooled to room temperature, and then 42 g of ammonium sulfate and 10.0 g of acetic acid was added to reduce the viscosity of the solution and to adjust the pH. The product of this reaction is a milky white liquid. The Reduced Specific Viscosity (RSV) of the product was 14.1 dL/g (0.125 M sodium nitrate, 30° C.).

Conditions for incorporation of the fluorescent monomer and the Reduced Specific Viscosities for a number of 35 mole percent cationic (65/25/10 mole ratio acrylamide/DMAEA-BCQ/DMAEA-MCQ) and 10 mole percent cationic (90/10 mole ratio acrylamide/DMAEA-BCQ) fluorescent dispersion polymers prepared in a fashion similar to Example 5 are summarized in Table I. The polymer products were precipitated in acetone, and then the precipitated polymer was dissolved in deionized water and analyzed for fluorescence using a Hitachi F-2000 fluorescence spectrophotometer. Tagged polymers C–H (Table 1) were typically several hundred times more fluorescent than untagged controls (A and B, Table I) under the conditions of analysis. Incorporation of the fluorescent tag into the high molecular weight fractions of the polymer products was also verified chromatographically, using a 20 cm×7.8 mm ID column packed in-house with Waters Accell Plus QMA packing. A mobile phase containing 1% acetic acid, 0.10 M sodium sulfate and 0.01 M tetrabutylammonium hydrogen sulfate was used to separate tagged high molecular weight polymer from low molecular weight polymer and residual fluorescent monomer, if present. A Waters 410 refractive Index detector and a Shimadzu RF-530 fluorescence detector were used simultaneously to quantitate incorporation and determine fluorescence relative to untagged controls.

TABLE I

Representative Fluorescent Cationic Dispersion Polymers

| Polymer | Mole % Cationic | Tag | % Tag by wt (based on monomer) | Conditions of Incorporation | RSV (dL/g) |
|---|---|---|---|---|---|
| A | 10 | none | — | — | 17.0 |
| B | 35 | none | — | — | 16.5 |
| C | 10 | 1 | 0.10 | 3 | 17.0 |
| D | 10 | 1 | 0.10 | 4 | 9.5 |
| E | 10 | 1 | 0.10 | 5 | 14.3 |
| F | 10 | 2 | 0.10 | 5 | 16.6 |
| G | 10 | 1 | 0.25 | 6 | 11.3 |
| H | 35 | 2 | 0.10 | 5 | 14.1 |

1 = DMAPMA-(7-acetoxy-4-bromomethylcoumarin) quaternary ammonium salt prepared according to Example 1.
2 = DMAEA-(6,7-dimethoxy-4-bromomethylcoumarin) quaternary ammonium salt prepared according to Example 2.
3 = Tag was added at 3 hours
4 = Tag was fed evenly into the polymerization over 4 hours
5 = Tag was added at 4 hours
6 = 50% of the tag was added at 3 hours; 50% of the tag was added at 4 hours

EXAMPLE 6

A fluorescent 90/10 mole percent DADMAC/DMAEA-BCQ solution copolymer was prepared by combining 262 g of diallyldimethyl ammonium chloride (DADMAC monomer, 62% aqueous solution), 42 g of dimethyaminoethyl acrylate benzyl chloride quaternary salt (DMAEA-BCQ), 80% aqueous solution), 61 g sodium chloride, and 100 mg of the appropriate fluorescent monomer prepared according to the procedure described in Example 1. This mixture was heated to 50° C., and purged with nitrogen. Six hundred milligrams of VA-044 (2,2' Azobis (N,N'-dimethyleneisobutyramidine)dihydrochloride, available from Wako Chemicals USA, Inc.; Richmond, Va.) in 50 mL of water was added to the reaction mixture at the rate of 11 mL/hour. After thirty minutes, 250 g of deionized water containing 900 mg of the fluorescent monomer was added to the reaction mixture at the rate of 50 mL/hour. After 5.5 hours, 0.60 g of VA-044 in 10 g of deionized water was added, and the reaction mixture was heated to 80° C. for three hours. After this time, 313 g of deionized water was added to the reaction mixture and the batch was cooled to room temperature. The product of the reaction is an opaque white liquid with a bulk viscosity typically around 10,000 cP. The fluorescent tag was present at 0.200 mole percent based on total monomer.

EXAMPLE 7

A low molecular weight fluorescent solution polymer of partially neutralized acrylic acid was prepared by combining 64 g of deionized water, 450 g of acrylic acid, 22.50 g of sodium hydroxide (50%) and 1.5 g of the fluorescent monomer synthesized according to the procedure in Example 1. This mixture was heated to 70° C. and purged with nitrogen for thirty minutes with vigorous mixing. Eight grams of ammonium persulfate was dissolved in 23 g of deionized water, and 79 g of sodium bisulfite was dissolved in 197 g of deionized water. The ammonium persulfate solution was added to the reaction mixture at the rate of 12 mL/hour, and the sodium bisulfite solution was added to the reaction mixture at the rate of 102 mL/hour. After 3.5 hours, 155 g of deionized water was added, and the reaction mixture was cooled to room temperature. The product was a clear yellow solution with a Brookfield viscosity of 1500 cP. The fluorescent tag was present at 0.050 mole percent based on total monomer.

EXAMPLE 8

A fluorescent emulsion polymer (Polymer I) was synthesized in the following manner.

An aqueous monomer phase solution was made-up by stirring together 0.0064 g of the DMAPMA-4-(bromomethyl)-6,7-dimethoxycoumarin quaternary salt (prepared according to Example 1), 13.1 g of a 47.5% aqueous solution of acrylamide, 0.45 g of adipic acid, 1.35 g of NaCl, 9.2 g of a 79.3% aqueous solution of DMAEA-MCQ, 7.8 g of water, and 0.18 g of a 5% aqueous solution o of EDTA.4Na$^+$. The components were stirred until in solution.

An oil phase was prepared by heating a mixture of 11.7 g of paraffinic oil, 0.94 g of POE(4) sorbitan monostearate (TWEEN® 60, available from ICI) and 0.41 g of sorbitan monooleate until the surfactants dissolved (54–57° C.).

The oil phase was charged into a 125 mL baffled reaction flask, and heated to 45° C. with vigorous stirring, the monomer phase was added dropwise over 2 min. The resulting mixture was stirred for 90 min.

To the water-in-oil emulsion was added 0.0139 g of AIBN (2,2'-azobis(isobutyronitrile), available from E. I. duPont Nemours & Co., Inc.; Wilmington, Del.) and 0.0010 g of AIVN (2,2'-azobis(2,4-dimethylvaleronitrile), available from E. I. duPont Nemours Co. Inc.; Wilmington, Del.). The polymerization was carried out under a $N_2$ atmosphere for 4 hours at 45° C., then 57° C. for one hour. An RSV of 11.3 dl/g (1M $NaNO_3$, 450 ppm, 30° C.) was measured for the resulting polymer. Polymers J–Q of Table II were similarly synthesized.

TABLE II

Representative Fluorescent Cationic Emulsion Polymers

| Polymer | Mole % DMAEA* MCQ | Tag Mole % | Viscosity Data RSV[4] | Comments |
|---|---|---|---|---|
| I | 30 | 0.0109[1] | 11.3 | Br counterion |
| J | 30 | 0.055[1] | 3.5 | Br counterion |
| K | 30 | 0.0060[1] | 12.8 | Cl counterion |
| L | 30 | 0.0118[1] | 13.3 | Cl counterion |
| M | 30 | 0.060[1] | 2.5 | Cl counterion |
| N | 10 | 0.050[1] | 3.4 | Cl counterion |
| O | 30 | 0.040[2] | 12.1 | Br counterion |
| P | 30 | 0.012[3] | 16.7 | Br counterion |
| Q | 30 | — | 20.0 | Control |

[1] = DMAPMA-(4-bromomethyl)-6,7-dimethoxycoumarin quaternary monomer prepared according to the procedure in Example 1.
[2] = DMAPMA-3-(bromomethyl)-6,7-dimethoxy-1-methyl-2(1H)-quinoxazolinone quaternary monomer prepared according to the procedure in Example 3.
[3] = DMAPMA-5-(bromomethyl)fluorescein quaternary monomer prepared according to the procedure in Example 4.
[4] = (450 ppm, 1M $NaNO_3$, 30° C.)

EXAMPLE 9

The utility of tagged dispersion polymers in monitoring polymer location and in dosage control was demonstrated utilizing polymer H (Table I) to dewater sludge from a midwestern municipal wastewater treatment facility.

A free drainage test is performed to evaluate the dewatering performance of tagged polymers. A 1 weight percent solution of the tagged polymer product to be tested was prepared. 200 mL of the sludge was placed in a 500 mL graduated cylinder. Different amounts of the tagged polymer solution were next added to the sludge. The graduated cylinder was then inverted to flocculate the particles in the sludge, then the contents of the graduated cylinder were gravity filtered through a fabric filter and the effluent drainage for a given time (usually 10 seconds) was recorded. A more effective flocculant is indicated by a higher volume of effluent which is able to pass through the filter in the given time. The effluent collected was retained for fluorescence analysis.

For this experiment, the fluorescence was analyzed directly using a Hitachi F-4500 fluorescence spectrophotometer. An increase in measured fluorescence was observed over the background just after the optimal polymer dosage was reached. The results are illustrated in Table III. Calibration curves for these polymers developed on a fluorescence spectrophotometer in the sludge matrix could be generated to allow a conversion from relative fluorescence (over background) to ppm polymer, if desired. This experiment shows that the polymers of the instant invention can be utilized to determine when the optimal amount of treatment flocculant has been added. In Table III, above a dosage of 8 ml of polymer, a large increase in fluorescent intensity is evident. Since the marked increase in measured fluorescence occurs just after the polymer dosage which is optimal for drainage (after which further increases in polymer dosage produce little or no increases in drainage volume), the use of the tagged polymers in this situation represents an indirect method for correlating polymer dosage to optimum drainage. The ability to exploit this effect has practical implications for optimizing various sludge dewatering processes and programs by providing a means to correlate polymer dosage to maximum drainage. There are also obvious economic benefits associated with the ability to determine when an overdose of the polymer is occurring, that is to say that more polymer is being applied than is required for efficient drainage. Such a determination could be made by monitoring the relative changes in fluorescence in the effluent for the present example.

TABLE III

Polymer Detection after Municipal Sludge Dewatering

| Polymer[1] dosage (mL) | Drainage[2] (ml) | Fluorescence Intensity[3] |
|---|---|---|
| 5.0 | 79.4 | 170 |
| 6.0 | 98.4 | 180 |
| 7.0 | 116.9 | 185 |
| 8.0 | 117.0 | 175 |
| 9.0 | 118.2 | 270 |
| 10.0 | 123.1 | 280 |

[1] = 35 mole % cationic (65/25/10 mole ratio acrylamide/DMAEA-BCQ/DMAEA-MCQ tagged with 0.10 weight percent (based on monomer) of DMAEA-(6,7-dimethoxy-4-bromomethylcoumarin) quaternary salt synthesized according to the method of Example 5.
[2] = how much supernatant flows through a filter 10 seconds after treatment with polymer
[3] = EX/EM = 345/431 nm

EXAMPLE 10

The utility of fluorescently tagged polymers for the correlation of optimal polymer dosage with turbidity reduction in pulp and paper applications was also demonstrated for paper furnish retention uses with a synthetic alkaline fine paper furnish (70% hardwood kraft/softwood kraft (60/40), 30% calcium carbonate) using polymers C and H (Table I).

A standard Britt jar experiment was used to evaluate the retention activity of tagged dispersion polymers in a paper furnish. The appropriate concentration of polymer was prepared to give a convenient dosage, such as 1 ml=0.2 lb/ton. The Britt jar test conditions for a typical experiment are given below:

Furnish: Standard Alkaline Furnish (500 ml)
Consistency: 0.5%
Jar: Standard three vaned
Screen: 100 R
Drainage Rate: 90–100 ml/30 sec
RPM: 500
Polymer Conc: 0.025 wt % (actives)
Polymer Dose: 0–3 1b (active)/ton In Britt jar retention experiments with synthetic standard alkaline furnish, with both polymers C and H (Table I) prepared according to the procedure of Example 5 an increase in fluorescence over background as a function of polymer dosage was observed. These data are shown in Tables IV and V. The turbidity of the filtrate was measured at 450 nm on a Hach DR-2000 Spectrometer. The filtrate collected was retained for fluorescence analysis.

In Tables IV and V, beyond a polymer dosage of 8 pounds per ton (on a product basis), a marked increase in fluorescence of the filtrate is observed, while little improvement in the reduction of the turbidity is evident. Therefore, by using the tagged polymers to monitor changes in the fluorescence of the filtrate as a function of polymer dosage, one obtains the ability to optimize the polymer dosage for a specific parameter of interest, in this case, the reduction of filtrate turbidity.

TABLE IV

Polymer Detection in Standard Alkaline Furnish

| Polymer[1] dosage (lb/ton) | % Turbidity Reduction | Fluorescence Intensity[2] |
|---|---|---|
| 0 | 0 | 50 |
| 2 | 51.1 | 55 |
| 4 | 78.9 | 58 |
| 8 | 86.7 | 65 |
| 12 | 89.0 | 80 |
| 16 | 86.4 | 85 |

[1] = 10 mole % cationic (90/10 mole ratio acrylamide/DMAEA-BCQ) tagged with 0.10 weight percent (based on monomer) of DMAPMA-(7-acetoxy-4-bromomethylcoumarin) quaternary salt synthesized in a fashion similar to the method of Example 5.
[2] = EX/EM = 320/452 nm

TABLE V

Polymer Detection in Standard Alkaline Furnish

| Polymer[1] Dosage (lb/ton) | % Turbidity Reduction | Fluorescence Intensity[2] |
|---|---|---|
| 0 | 0 | 45 |
| 2 | 47.4 | 45 |
| 4 | 77.3 | 45 |
| 8 | 89.2 | 50 |
| 12 | 82.8 | 53 |
| 16 | 85.8 | 60 |

[1] = 35 mole % cationic (65/25/10 mole ratio acrylamide/DMAEA-BCQ/DMAEA-MCQ tagged with 0.10 weight percent (based on monomer) of DMAEA-(6,7-dimethoxy-4-bromomethylcoumarin) quaternary salt synthesized according to the method of Example 5.
[2] = EX/EM = 345/431 nm

EXAMPLE 11

The standard free drainage test described in Example 9 was utilized to test the polymers of the instant invention in sludge from chemical processing waste water.

Specifically, polymer H (Table I) synthesized according to the procedure of Example 5 was used to dewater the CPI sludge from a midwestern chemical processing facility. Fluorescence data obtained from analysis of the supernatants from the sludge is shown in Table VI. The increase in measured fluorescence in the supernatant with increasing drainage correlates to polymer dosage. In this example, the relative changes in measured fluorescence intensity observed in the effluent as polymer dosage is increased become significantly smaller after the most efficient polymer dosage is applied (4 mL). Thus, the onset of these decreasing differences in measured fluorescence could be used to indicate the optimal polymer dosage for drainage.

TABLE VI

Polymer Detection After CPI Sludge Dewatering

| Polymer[1] dosage (mL) | Drainage (10 sec) | Fluorescence Intensity[2] |
|---|---|---|
| 0 | — | 1513 |
| 2.0 | 95.5 | 1628 |
| 2.5 | 113.5 | 1751 |
| 3.0 | 139.3 | 1788 |
| 4.0 | 155.5 | 1820 |
| 5.0 | 155.6 | 1885 |
| 6.0 | 156.5 | 1898 |

[1] = 35 mole % cationic (65/25/10 mole ratio acrylamide/DMAEA-BCQ/DMAEA-MCQ tagged with 0.10 weight percent (based on monomer) of DMAEA-(6,7-dimethoxy-4-bromomethylcoumarin) quaternary salt synthesized according to the method of Example 5.
[2] = EX/EM = 345/431 nm Changes can be made in the composition, operation and arrangement of the method of the present invention described herein without departing from the concept and scope of the invention as defined in the following claims:

We claim:

1. A cationic water-soluble polymer comprising from 0.001 to 10 mole percent of a repeating mer unit represented by the formula

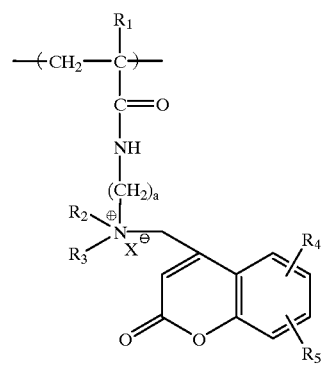

wherein a is an integer of from 1 to 10, $R_1$ is selected from the group consisting of hydrogen and methyl groups, $R_2$ and $R_3$ are methyl groups, $R_4$ and $R_5$ are selected from the group consisting of hydrogen, hydroxy, methoxy, ethoxy, amino, dimethylamino, diethylamino and acetoxy groups, and X is selected from the group consisting of chloride, iodide and bromide ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quaternary salt, dimethylaminoethyl acrylate benzyl chloride quaternary salt, diallyldimethyl ammonium chloride, N-vinyl formamide, dimethylaminoethyl methacrylate methyl chloride quaternary salt, dimethylaminoethyl methacrylate benzyl chloride quaternary salt, methacrylamidopropyl trimethyl ammonium chloride and acrylamidopropyl trimethyl ammonium chloride.

2. The polymer of claim 1 wherein a is an integer of from 2–4.

3. The polymer of claim 1 wherein the polymer is selected from the group consisting of emulsion, solid, dispersion and solution polymers.

4. A cationic water-soluble polymer comprising from 0.001 to 10 mole percent of a repeating mer unit represented by the formula

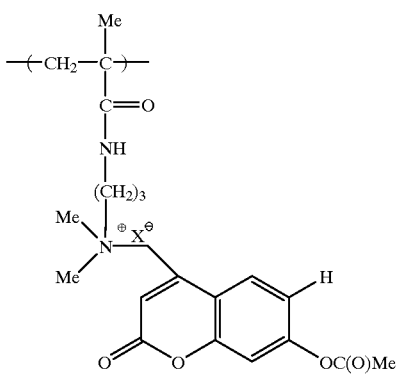

wherein X is selected from the group consisting of bromide, iodide and chloride ions and wherein the polymer also contains from 90 to 99.999 mole percent of a remaining portion of randomly distributed vinylic mer units selected from at least one of the monomer groups consisting of acrylamide, acrylic acid, methacrylamide, vinyl acetate, dimethylaminoethyl acrylate methyl chloride quatemnary salt, dimethylaminoethyl acrylate benzyl chloride quatemnary salt, diallyldimethyl ammonium chloride, N-vinyl formamide, dimethylamninoethyl methacrylate methyl chloride quaternary salt, dimethylaminoethyl methacrylate benzyl chloride quaternary salt, methacrylamidopropyl trimethyl ammionium chloride and acrylamidopropyl trimethyl ammonium chloride.

5. The polymer of claim 4 wherein the polymer is selected from the group consisting of emulsion, solid, dispersion and solution polymers.

* * * * *

UNITED STATES PATENT AND TRADEMARK OFFICE
CERTIFICATE OF CORRECTION

PATENT NO. : 5,986,030
DATED : November 16, 1999
INVENTOR(S) : Patrick G. Murray and Wesley L. Whipple It is certified that error appears in the above-identified patent and that said Letters Patent is hereby corrected as shown below:

COLUMN 26, CLAIM 4, LINE 7 and 8
    quatemnary
SHOULD READ AS:
    quaternary
COLUMN 26, CLAIM 4, LINE 10
    dimethylamninoethyl
SHOULD READ AS:
    dimethylaminoethyl
COLUMN 26, CLAIM 4, LINE 13
    ammionium
SHOULD READ AS:
    ammonium IN THE ABSTRACT, LINES 6, 20, 26
    fluor
SHOULD READ AS:
    Fluor Signed and Sealed this Third Day of April, 2001

Attest:

NICHOLAS P. GODICI

Attesting Officer      Acting Director of the United States Patent and Trademark Office